United States Patent
Nowak et al.

(10) Patent No.: US 9,050,158 B2
(45) Date of Patent: Jun. 9, 2015

(54) METHOD FOR ACQUIRING THREE-DIMENSIONAL IMAGES

(75) Inventors: Christoph Nowak, Vienna (AT); Horst Koinig, Klagenfurt (AT)

(73) Assignee: A. TRON3D GMBH, Klagendfurt am Worthersee (AT)

( * ) Notice: Subject to any disclaimer, the term of this patent is extended or adjusted under 35 U.S.C. 154(b) by 573 days.

(21) Appl. No.: 13/500,979

(22) PCT Filed: Oct. 6, 2010

(86) PCT No.: PCT/AT2010/000372
§ 371 (c)(1),
(2), (4) Date: May 16, 2012

(87) PCT Pub. No.: WO2011/041812
PCT Pub. Date: Apr. 14, 2011

(65) Prior Publication Data
US 2012/0218389 A1    Aug. 30, 2012

(30) Foreign Application Priority Data
Oct. 7, 2009    (AT) .................................. A 1585/2009

(51) Int. Cl.
*H04N 13/02*    (2006.01)
*A61C 19/04*    (2006.01)
*G06T 7/00*    (2006.01)

(52) U.S. Cl.
CPC .................. *A61C 19/04* (2013.01); *G06T 7/002* (2013.01); *G06T 7/0057* (2013.01); *G06T 7/0075* (2013.01); *G06T 2207/10012* (2013.01); *G06T 2207/30036* (2013.01)

(58) Field of Classification Search
None
See application file for complete search history.

(56) References Cited

U.S. PATENT DOCUMENTS

| 7,426,317 B2 | 9/2008 | Nielsen |
| 7,542,033 B2 | 6/2009 | Kawakami et al. |

(Continued)

FOREIGN PATENT DOCUMENTS

| JP | 2001194114 A | 7/2001 |
| JP | 2001194126 A | 7/2001 |

(Continued)

OTHER PUBLICATIONS

Scharstein, et al., "High-accuracy stereo depth maps using structured light", Proceedings 2003 IEEE Computer Society Conference on Computer Vision and Pattern Recognition, Jun. 18-20, 2003, pp. 195-202, Madison, Wisconsin, URL: http://research.microsoft.com/pubs/75606/scharstein-cvpr03.pdf.

(Continued)

*Primary Examiner* — Christopher S Kelley
*Assistant Examiner* — Kaitlin A Retallick
(74) *Attorney, Agent, or Firm* — Laurence A. Greenberg; Werner H. Stemer; Ralph E. Locher

(57) ABSTRACT

A method for acquiring three-dimensional images of objects uses two cameras having acquisition areas that overlap each other. In the course of a calibration method, a group of epipolar lines associated with each other is determined for each of the cameras. A specified random image is projected onto the object to be imaged. For each pixel of the camera, a first environment is determined, an associated first epipolar line is determined, and for the first epipolar line an associated second epipolar line of the second camera is determined. For all pixels of the image of the second camera that are located on the second epipolar line, a second environment congruent to the first environment is determined. The intensity values of the first and the second environments are compared with each other and a measure of agreement is calculated. A spatial position is determined by use of the previously determined transformation.

15 Claims, 2 Drawing Sheets

(56) References Cited

U.S. PATENT DOCUMENTS

| | | | |
|---|---|---|---|
| 2007/0081718 A1* | 4/2007 | Rubbert et al. | 382/154 |
| 2007/0098264 A1 | 5/2007 | Van Lier et al. | |
| 2007/0128580 A1* | 6/2007 | Mormann | 433/201.1 |
| 2007/0165243 A1* | 7/2007 | Kang et al. | 356/603 |
| 2009/0169095 A1* | 7/2009 | Zhuang et al. | 382/154 |
| 2010/0283781 A1 | 11/2010 | Kriveshko et al. | |
| 2011/0007137 A1 | 1/2011 | Rohaly et al. | |
| 2011/0007138 A1 | 1/2011 | Zhang et al. | |
| 2011/0043613 A1 | 2/2011 | Rohaly et al. | |
| 2011/0164810 A1 | 7/2011 | Zang et al. | |

FOREIGN PATENT DOCUMENTS

| | | |
|---|---|---|
| JP | 2002013918 A | 1/2002 |
| JP | 2003256865 A | 9/2003 |
| KR | 1020040065525 A | 7/2004 |
| KR | 1020060100376 A | 9/2006 |
| WO | 2009/089126 A1 | 7/2009 |

OTHER PUBLICATIONS

Seales, et al., "Realtime-depth warping for 3-d scene reconstruction", Proceedings Aerospace Conference, Mar. 1999, pp. 413-419, vol. 3, Snowmass at Aspen, Colorado, USA, URL: http://research.microsoft.com/pubs/75606/scharstein-cvpr03.pdf.

Kang, et al., "A Multibaseline Stereo System with Active Illumication and Real-time Image Acquisition", Proceedings IEEE Fifth International Conference on Computer Vision, 1995, pp. 88-93, URL: http://research.microsoft.com/en-us/um/people/larryz/kang__sing_bing_1995_1.pdf.

Yamaguchi, Jun'ichi, "Optical Techniques for Human Sensing" Journal of the Society of Instrument and Control Engineers, The Society of Instrument and Control Engineers, published Apr. 10, 2000, vol. 39, pp. 273-278—English abstract.

* cited by examiner

METHOD FOR ACQUIRING THREE-DIMENSIONAL IMAGES

BACKGROUND OF THE INVENTION

1. Field of the Invention:

The present invention relates to a method according to the preamble of claim 1 for capturing three-dimensional images of objects as well as to an assembly according to the preamble of claim 8 for capturing three-dimensional images of objects.

Methods and assemblies of the invention will particularly be used for providing three-dimensional images of teeth. The areas of use cover the provision of digital teeth and jaw impressions, the provision of diagnostic aids, monitoring dental treatments and the implementation of reliable check-ups of implants. Apart from other areas of use in the fields of medical and industrial technology, for example for endoscopies, it is generally possible to use said method and assembly for stereometric measurements of areas which are difficult to access.

The acquisition of stereometric images of areas which are difficult to access, for example of teeth in the oral cavity of human beings, constitutes the background of the present invention. The difficulties in this connection consist in the required miniaturization of the capturing unit, on the one hand, and in the required high reliability of the method, on the other hand. Particularly in the area of dentistry, dimensions of about 0.1 mm may be of relevance, so that a resolution in the range of about 0.01 mm is required in order to be able to record all the details of the objects to be imaged at a sufficiently high resolution.

According to the state of the art, dental measuring devices for capturing three-dimensional images are known. A significant disadvantage of these devices consists in the mostly unhandy and bulky dimensions of the sensor parts which are advanced to the objects to be imaged, as a high number of different components may be required in the image area.

BRIEF SUMMARY OF THE INVENTION

The task of the present invention, thus, consists in providing an assembly and a method for providing highly precise three-dimensional images, said assembly having as compact a configuration as possible.

According to the invention the arrangement of both cameras is pre-calibrated, the positions and orientations of the cameras in relation to one another being determined and a transformation which assigns exactly one position in space in a three-dimensional capturing space to each image position of an image recorded with one of the cameras and to each image position of an image recorded with the other camera being established. In the course of the calibrating procedure, a plurality of epipolar lines is determined for each of the cameras, one epipolar line of the one camera being assigned to one epipolar line of the other camera. It is provided that a predetermined random image is projected onto the object to be imaged, the individual picture points of the random image having at least one of two different color values and/or intensity values. After that, a first neighborhood is determined for each pixel of the first camera, and an epipolar line determined for the first camera and comprising the respective pixel is established. Then the second epipolar line of the second camera, which is assigned to said first established epipolar line, is determined. A second neighborhood, which is congruent to the first neighborhood, is determined for all the pixels of the image of the second camera located on said second epipolar line; the intensities of the first and second neighborhoods are compared; the degree of consistency of the two neighborhoods is determined, and the image position on the second epipolar line with the highest consistency is located. The transformation is used to determine a position in space based on the position of the pixel of the first camera in the image and the established position of the second epipolar line; this position in space is stored, the image of the imaged object being determined by the set of determined positions in space and being made available for further processing. This procedure allows for simple and efficient capturing of three-dimensional images and imaging of objects, the assignment of two pixels of the two cameras depicting the same pixel area is much easier than in previous methods, and the calculations for locating two pixels depicting the same image area are significantly accelerated.

A special embodiment of the present invention provides for an inactivation of the projection of the random image immediately before or after the set of positions in space are/have been recorded and for an optional additional illumination of the object, at least one camera capturing an image. The respective intensity or image position is assigned to each of the determined points in space, based on which the position in space of said points can be determined using the transformation. This procedure allows for the recorded three-dimensional images of the object to be represented in color, optionally in their original colors.

It may also be provided for a partitioning of the surface or the space using a meshing method based on the recorded set of points and using a number of spatial elements or surface elements. This constitutes an advantage as the recorded set of points may easily be three-dimensionally represented and it is easy to carry out subsequent calculations.

A special aspect of the invention provides that an intensity value determined based on the intensity values of the points in space of the set of points is assigned to the surface elements of the sectioned surface, particularly by interpolation, and is optionally displayed. This allows for a particularly realistic representation of the colors of the imaged objects.

A particularly advantageous aspect of the present invention provides that three-dimensional images of objects are continuously recorded, while the objects are moved in relation to the camera assembly, the relative movement of the objects being sufficiently slow so that the areas recorded in subsequent images overlap, and that the determined set of points, the sectioned surfaces or the sectioned spaces are aligned by means of isometric transformation. It is, thus, possible to create an assembled image based on a plurality of images. It is advantageous that the images, which are normally taken from a very small distance, may be assembled easily in order to create an overall image consisting of several partial images, the size of said overall image being greater than that of the image area of the two cameras.

It may also be provided that, in case of lacking consistency between the first neighborhood and the second neighborhoods of the pixels on an epipolar line of the image recorded by the second camera, an anti-shine fluid is sprayed onto the surface of the objects to be imaged, and that the procedure of locating consistent neighborhoods is continued after having sprayed on said fluid. This allows for obtaining precise three-dimensional images, particularly in case objects having a strongly reflecting or very smooth surface.

Moreover, in an assembly for capturing three-dimensional images of objects using two cameras which have overlapping image areas, a projection unit for projecting a random image is provided according to the invention, so that the individual pixels of the random image have one of at least two different color and/or intensity values, the random image being projectable into the overlapping image areas of the two cameras of the projection unit. In this assembly, it is provided that the random image is selected in a way that the pixels situated on the same epipolar line 9a, 9b (shown in FIG. 3) in the image areas of the two cameras 1a, 1b (shown in FIG. 1) have distinct neighborhoods. Such an assembly allows for capturing images which may easily be converted into a three-dimensional image.

A special aspect of the present invention provides a light source which is preferably switchable and illuminates the overlapping image areas of the two cameras. Thanks to the illumination using said light source, further images may be taken in addition to the images required for capturing the three-dimensional images; said further images may be viewed immediately or used for coloring a three-dimensional image of an object after capturing.

Moreover, the invention may be further developed by means of an atomizer which may be used for spraying an anti-shine fluid onto the objects to be imaged. This allows for capturing matt images which makes it easier to obtain a three-dimensional image.

A further preferred aspect of the invention provides that a calibrating unit is post-positioned to the cameras, said calibrating unit determining the positions and orientations of the two cameras in relation to one another and establishing a transformation which assigns exactly one position in space, particularly one voxel, in a three-dimensional image space to one image position, particularly one pixel, of an image captured by one of the two cameras and to an image position, particularly one pixel, of an image captured by the other camera and determining a family of epipolar lines for each of the cameras, one epipolar line of one camera being assigned to exactly one epipolar line of the other camera; that an evaluation unit is post-positioned to the cameras, said evaluation unit determining a first neighborhood, for example consisting of 3×3 or 5×5 pixels, for each pixel of the first camera, determining a first epipolar line determined for this first camera and comprising the respective pixel, determining the second epipolar line of the other camera assigned to said determined first epipolar line, a second neighborhood, congruent in relation to said first neighborhood, being determined for all the pixels of the image captured by the second camera which are located on said second epipolar line, the intensity values of the first and second neighborhoods being comparable by means of a comparing unit, said comparing unit determining the degree of consistency of the two neighborhoods and those image positions, particularly the pixel, on the second epipolar line with the highest degree of consistency, the transformation being used for determining a position in space based on the image position of the pixel of the first camera and the determined image position on the second epipolar line, said position in space being storable in a memory.

Such an assembly allows for capturing three-dimensional images of objects in a simple and cost-efficient way.

It may also be provided that the optical axes of the two cameras are almost parallel. This allows for an easy determination of the transformation and improves the precision of the captured three-dimensional images.

Another advantageous aspect of the invention provides that the two cameras and the projection unit are arranged on the same support or instrument. This allows for an easy handling, particularly when only little space is available.

Advantageous versions and further developments of the invention are described in the dependent claims.

The invention will be exemplarily described referring to the following figures.

DESCRIPTION OF THE INVENTION

Figure 1:
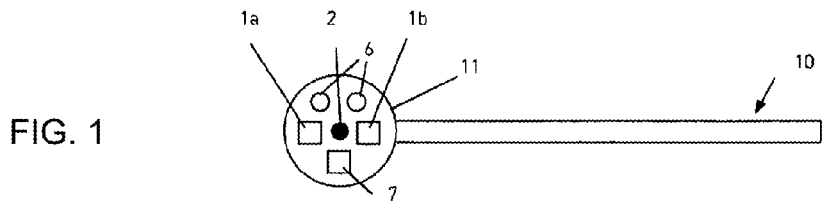
FIG. 1 shows a front view of an instrument having the form and dimensions of a dental mirror and two cameras and a projection unit.

FIG. 1 shows an example of the basic configuration of an assembly of the invention with an instrument 10 having the form and the dimensions of a dental mirror. This assembly comprises an instrument 10, two cameras 1a, 1b and a projection unit 2 being arranged on the terminal unit 11 of said instrument 10. Alternative embodiments may comprise endoscopes, surgical instruments, or instrument heads in general, which are able to reach the inaccessible objects 30 to be imaged, such as teeth, and on which two cameras 1a, 1b and a projection unit 2, which will be described below, can be arranged.

Figure 2:
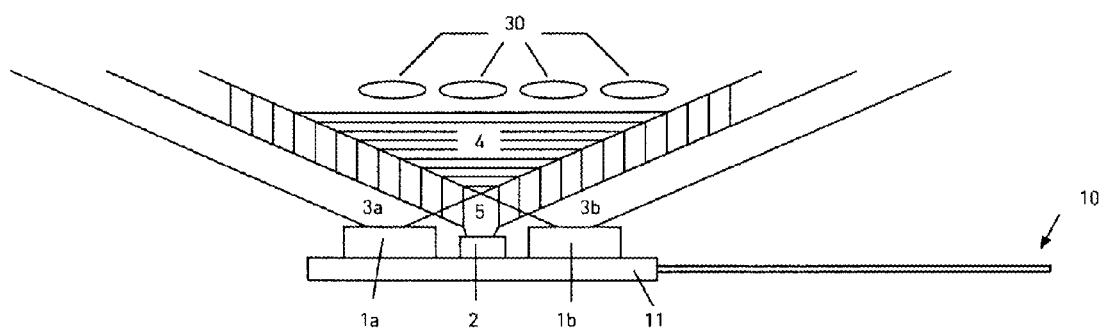
FIG. 2 shows a lateral view of the instrument having two cameras and a projection unit.

These two cameras 1a, 1b have partly overlapping image areas 3a, 3b (shown in FIG. 2). The image areas of the two cameras 1a, 1b are selected to be of the same size; depending on the typical distance of the cameras 1a, 1b from the objects 30 to be imaged, the image areas are selected so that as large a part of the objects 30 as possible is situated in the overlapping areas 4 of the image areas 3a, 3b of the two cameras 1a, 1b.

Figure 8:
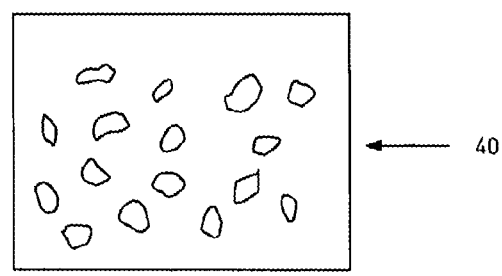
FIG. 8 shows a random image.

In the area between the two cameras 1a, 1b, a projection unit 2, which projects a random image 40 (shown in FIG. 8) into at least a partial area of the overlapping areas 4 of the two cameras 1a, 1b, is located. It is particularly advantageous to project the random image 40 onto the overall overlapping areas 4 of the two image areas 3a, 3b of the two cameras 1a, 1b. In the example shown in FIG. 2, the random image 40 is projected into a projection area 5, comprising the overlapping area 4 of the two image areas 3a, 3b of the two cameras 1a, 1b, by means of the projection unit 2.

Figure 3:
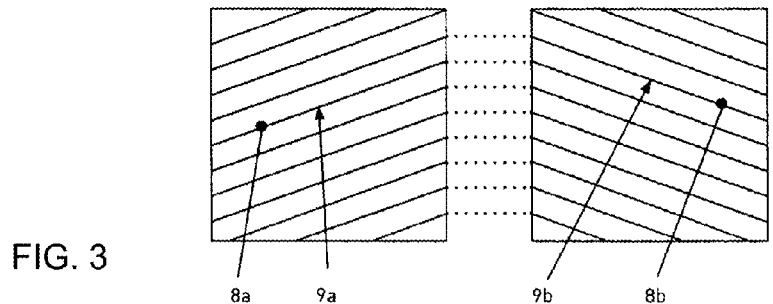
FIG. 3 shows images of the two cameras and the epipolar lines assigned to one another.
Figure 7:
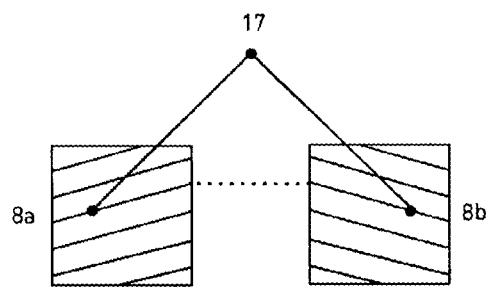
FIG. 7 shows the effect of a calibrated transformation function in the case of two given image positions on the images produced using the two cameras.

Before images of the objects are captured, the positions of the two cameras 1a, 1b are calibrated. The projection unit 2 is not needed for calibrating the two cameras 1a, 1b and may remain switched off during the entire calibrating procedure. The calibrating procedure at first determines the positions and orientations of the two cameras 1a, 1b in relation to one another. There are different ways of implementing this procedure, an advantageous way being described in J. Heikkilä, Geometric camera calibration using circular control points, IEEE Transactions on Pattern Analysis and Machine Intelligence 22(10), 1066-1077, 2000 or in Faugeras, Toscani, Camera calibration for 3D computer vision, Proc. Int'l Workshop on Industrial Applications of Machine Vision and Machine Intelligence, Tokyo, Japan, pp. 240-247, February 1987. A transformation is obtained as a result, said transformation assigning a point 17 (shown in FIG. 7) in space within the overlapping image area of the two cameras 1a, 1b a picture point 8a (shown in FIG. 3) of an image captured by the first camera 1a and to a picture point 8b of an image captured by the second camera 1b.

A picture point 8a, 8b is assigned bijectively to each pixel on a one-to-one basis. Picture points may, however, also be located between the individual pixels, which is why the method described below is suited for the application of sub-pixel arithmetic.

Of course, it is not possible to assign any picture point 8a, 8b to a pixel, but it is only possible to determine a point 17 in space for those picture points 8a, 8b which are situated on epipolar lines 9a, 9b which are assigned to one another. For this reason, it is required in connection with calibration to determine a family of epipolar lines 9a, 9b (shown in FIG. 3) of the two cameras 1a, 1b and to assign bijectively one epipolar line 9b of one camera to each of the epipolar lines 9a of the other camera 1a. Methods for determining and assigning the epipolar lines 9a, 9b to one another are known to those of skilled in the art and described, for example, in Zhengyou Zhang, Determining the Epipolar Geometry and its Uncertainty: A Review, International Journal of Computer Vision, Vol. 27, pp. 161-195, 1996.

As has already been mentioned, a random image 40 is projected onto the overlapping area 4 of the two cameras 1a, 1b in the course of the method of the invention. The random image may, for example, be a digital image having a predetermined height and width and a number of pixels or image areas which are arranged in a rectangular array. These pixels each have color and intensity values chosen from a number of preset color and/or intensity values. A random image 40 is used because for the method described below it is required that the neighborhood of each pixel, for example a neighborhood consisting of 3×3 or 5×5 pixels, may be clearly assigned to the respective pixel within the overall random image. Based on the clear assignment of the neighborhood, a point in space may be found in different locations in two digital images captured by one of the two cameras 1a, 1b. If two different light intensity values, such as black and white, are chosen as possible random values for one pixel, about 32 million different neighborhoods are possible when using neighborhoods consisting of 5×5 pixels, so that images of up to 32 million pixels may be captured without any limitations and a distinct neighborhood may be clearly assigned to each of the captured pixels.

The random image may be produced by simple means and may, for example, be available in the form of a slide. The individual random values assigned to each of the pixels may be calculated using a known algorithm, such as a Mersenne Twister algorithm which is known in the field of the invention and described in M. Matsumoto and T. Nishimura, Mersenne Twister: A 623-dimensionally equidistributed uniform pseudorandom number generator, ACM Trans. on Modeling and Computer Simulations, 1998.

Alternatively, in order to reduce the space required for the assembly, the projection unit 2 may be formed with a diffraction grating, the diffraction grating for information of a digital image having significantly smaller dimensions than if slides are used. The configuration of the diffraction gratings for the representation of digital images is known to those of skill in the art and is, for example, described in J R Leger, M G Moharam, and T K Gaylord, Diffractive Optics—An Introduction to the Feature Issue. Applied Optics, 34 (14), p. 2399-2400, 1995. In the area of the slide or the diffraction grating, a light source, such as a laser diode, is situated for projecting its light through the slide or the diffraction grating onto the objects 30.

In order to obtain a three-dimensional image of the object 30, the following steps are carried out individually for each pixel 8a of the images captured by one of the two cameras which will be referred to as the first camera 1a below. These pixel 8a captured by the first camera 1a will be referred to as first pixels 8a below. The number of these pixels 8a may optionally be reduced by the number of those pixels whose image areas are not part of the image area of the other camera which will be referred to as second camera 1b below. The pixels 8b captured by the second camera 1b will be referred to as second pixels 8b below.

Figure 4:
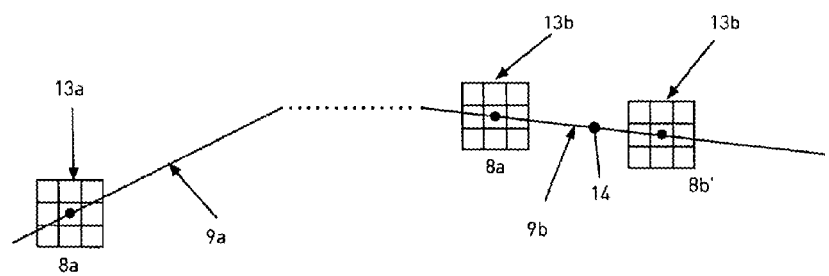
FIG. 4 shows a first epipolar line, a second epipolar line, and the points located on these epipolar lines and their respective neighborhoods.

At first, a first neighborhood 13a is determined for each of the first pixels 8a (shown in FIG. 4). The neighborhood 13a may, for example, be a neighborhood consisting of 5×5 pixels, the respective pixel 8a preferably being located at a central position of the first neighborhood 13a.

For each of the first pixels 8a of the first camera 1a, the epipolar line 9a, as shown in FIG. 4, of the first camera 1a and the epipolar line 9b of the second camera 1b assigned to said first epipolar line 9a are used. As has already been mentioned, these epipolar lines 9a, 9b have already been determined in the course of the calibration of the cameras 1a, 1b. Then, a second neighborhood 13b consisting of 5×5 pixels is determined for the second pixels 8b of the image captured by the second camera 1b which are located on the second epipolar line 9b; said second neighborhood 13b is then compared to the first neighborhood 13a. In the course of said comparison, the degree of consistency is determined, which shows whether the intensity values of the two neighborhoods 13a, 13b are consistent.

If the intensity values assigned to the two neighborhoods 13a, 13b are consistent, the degree of consistency will—depending on how it is formulated—be highest or lowest; in case of total consistency, it will particularly be zero. It is, for example, possible to use the Euclidian space as a measure of the consistency of two neighborhoods; in this case, all intensity values of the neighborhood will be compared pixel by pixel. Other methods for obtaining a degree of consistency can be found in Reinhard Klette, Andreas Koschan, Karsten Schlüns: Computer Vision—Räumliche Information aus digitalen Bildern, 1$^{st}$ edition, Friedr. Vieweg & Sohn Verlag, 1996.

Figure 5:
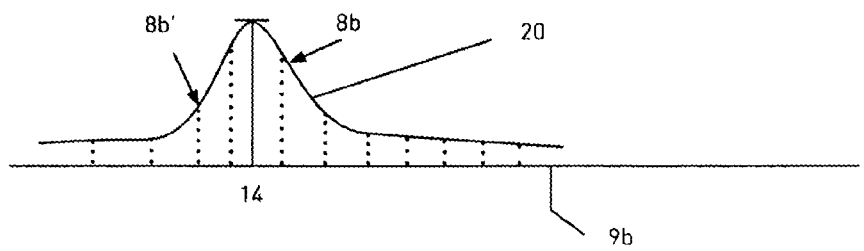
FIG. 5 shows a discrete image of the degree of consistency and an interpolation of the degree of consistency on one of the second epipolar lines.

The degree of consistency is determined for the respective neighborhoods 13a, 13b of two pixels, the first of which being located in the image captured by the first camera 1a and the other one on the second epipolar line 9b assigned to the first epipolar line 9a on which the first pixel 8a is located in the image captured by the first camera 1a. As there are typically 100 to 1,000 pixels on each of the second epipolar lines 9b, the degree of consistency for all points on the second epipolar line 9b is determined. These degrees of consistency are entered into a discretely defined functions together with the image position of the respective pixel, the area of definition of said functions being extended to the overall second epipolar line 9b by means of an interpolation function 20. This discretely defined function of the degrees of consistency and its assigned interpolating function 20 are shown in FIG. 5. The maximum of said interpolating function 20 is determined, and the image position 14 where the maximum is found is considered as the image position corresponding to the pixel 8a from the image captured by the first camera. It is assumed that this image position 14 and the image position of the pixel 8a from the image captured by the first camera 1a show the same section of the object, as their neighborhoods are very similar and clear in the image areas.

Thus, image positions of the image captured by the second camera 1b showing the same section of an object as a pixel of the image captured by the first camera 1a are only searched on the second epipolar lines 9b. This means that the strict criterion of the unambiguousness of the neighborhood may no longer be applied to the overall random image, instead requiring only the neighborhood of the pixel lying on the same epipolar line 9a, 9b in the images captured by the two cameras 1a, 1b to be unambiguous. Due to this extension of the area of the permissible random image, in most cases it is sufficient to determine a neighborhood of 3×3 pixels. For a higher reliability and precision, a neighborhood of 5×5 pixels which is numerically more complex can be used.

The two determined image positions are transformed in the course of the calibration, which yields a position 17 in space. This position 17 in space corresponds to the position in space which has been captured in the course of capturing in both determined image positions in the images captured by the two cameras.

If this procedure is applied to a number of image points 8a of an image captured by the first camera 1a, an equal number of image positions 14 in the image captured by the second camera at the same time and an equal number of points 17 in space on the surface of the captured object 30 are obtained.

A further development of the assembly of the invention is shown in FIG. 1, said assembly additionally having a switchable light source 6 which illuminates the objects 30 to be imaged in the overlapping area 4 of the image areas 3a, 3b of the two cameras. This light source 6 may be turned on as short a time as possible before turning on the projection unit 2. Then, one or both of the two cameras 1a, 1b capture an image, and the intensity values for one or several color channels are captured. After that, the light source 6 is turned off and the projection unit 2 is turned on and the above described procedure for determining the positions 17 in space is implemented. It is assumed that the position of the assembly remains unchanged between capturing the image using the light of the light source 6 and the subsequent capturing of the positions 17 in space. After having determined the image positions 14 and the respective points 17 in space, each point 17 in space may be assigned the intensity value of the pixel 8a determining it via the transformation and/or or the respective second pixel 8b on the second epipolar line 9b.

The procedure of the invention may be additionally improved by applying a meshing step to the determined point cloud of the determined points 17 in space after having determined said points. The determined points 17 in space are considered as points on the surface of a three-dimensional object represented by a tetrahedron. The object may optionally also be represented by other elements, such as prisms or cubes, or only the surface may be represented by triangles or rectangles. A comprehensive description of meshing algorithms may, for example, be found in Joe, Simpson, Triangular Meshes for Regions of Complicated Shape, International Journal for Numerical Methods in Engineering, Wiley, Vol. 23, pp. 751-778, 1986 or in Borouchaki, Lo, Fast Delaunay triangulation in three dimensions, Computer methods in applied mechanics and engineering, Elsevier, Vol. 128, pp. 153-167, 1995.

If intensity values have already been assigned to the individual points 17 in space before, the intensity values may be transferred to the surface elements by means of interpolation, which yields a continuous coloration of the surface.

Figure 6:
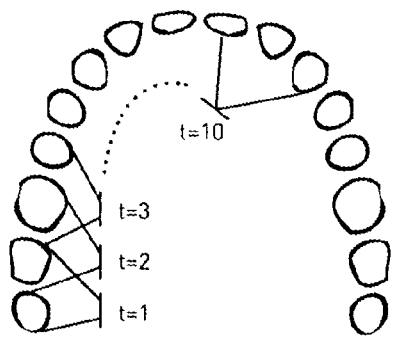
FIG. 6 shows an image of the teeth as an assembled image consisting of several individual images.

The assembly shown in the figures captures about ten to twenty images of the object 30 to be imaged per second. If the assembly is moved slowly in relation to the objects to be imaged (teeth in this case), as shown in FIG. 6, so that overlapping areas of the objects will be captured in two subsequent time steps, it is possible to convert the overlapping image areas by means of an isometric transformation into each other, so that they are situated in the same area in space. Such procedures are, for example, described in Timothée Jost, Heinz Hügli, Fast ICP algorithms for shape registration, Proceedings of the $24^{th}$ DAGM Symposium on Pattern Recognition, pp. 91-99, 2002. By taking several images at different points in time, a larger three-dimensional image may be assembled using several smaller images. This way, a three-dimensional image of the overall row of teeth shown in FIG. 6 may be obtained. In the course of the capturing process, the currently captured three-dimensional overall image is displayed on a monitor. The measuring process is additionally supported by an optimal positioning (virtual horizon) during the measuring, and the current position of the measuring head is represented in the respective three-dimensional image.

The improvement of the assembly of the invention described below results in an improved contrast in the images captured by the cameras. If the surface of the objects to be imaged is highly reflective, the images may not be correctly represented or may show some undesired reflections which significantly affect the quality of the images. For this reason, an anti-shine liquid, such as alginate, may be sprayed onto the teeth, making it significantly easier to capture three-dimensional images applying the described procedure. For this reason, the assembly is provided with an atomizer 7, which may be used to apply an anti-shine fluid on the objects to be imaged.

The handle of the instrument 10 supporting the assembly has a cable on its back side, said cable connecting the assembly to a processing unit. This processing unit supplies the cameras 1a, 1b, the projection unit 2, the light source 6 with supply voltage and receives the collected data from the cameras 1a, 1b. Moreover, the liquid may be supplied to the atomizer 7 via a liquid conduit through the handle of the instrument 10.

Alternatively, a WLAN interface may be used for transferring the data to the processing unit. A WLAN interface offers the advantage of no longer requiring any cables. In this embodiment, the instrument 10 is provided with a battery for supplying the cameras, the projection unit, and the light source with voltage and with a tank holding the anti-shine liquid.

Advantageously, it may be provided that the random image 40 is selected in a way that the pixels, located on the same epipolar line 9a, 9b in the images captured by the two cameras 1a, 1b, have distinct neighborhoods 13a, 13b.

Such a random image 40 differs from a known structured light pattern in that the neighborhoods 13a, 13b of the individual pixels are different from one another and, particularly, are unique on an epipolar line 9a, 9b. Structured light patterns comprise a plurality of pixels having identical neighborhoods 13a, 13b. Contrary to the structured light patterns, it is possible to carry out a recognition procedure in order to recognize identical points in space in the images captured by the cameras in a single capturing step. This is particularly advantageous, as movement artifacts which are produced if several subsequent images using several structured light patterns are captured can be avoided. Thus, a faster and simpler detection of three-dimensional images is made possible.

The invention claimed is:

1. A method for capturing three-dimensional images of objects using two cameras having overlapping image areas, wherein a configuration of the two cameras being pre-calibrated, which comprises the steps of:
   determining positions and orientations of the two cameras relative to one another;
   establishing a transformation, the transformation assigning exactly one position in space, namely one voxel, in a three-dimensional image space to a first image position, namely a position of a pixel, of an image captured using a first of the cameras and a second image position, being a position of a pixel, of an image captured using a second of the cameras;
   determining, during a course of a calibrating procedure, a family of epipolar lines for each of the cameras, exactly one epipolar line of the second camera being assigned to each of the epipolar lines of the first camera;
   projecting a predetermined random image onto an object to be imaged, individual pixels of the predetermined random image having one of at least two different color values and/or intensity values and in that then, for each pixel of the first camera:
   determining a first neighborhood;
   determining a first epipolar line for the first camera and containing a respective pixel;
   assigning a second epipolar line of the second camera to the first epipolar line determined;
   performing the following steps for each pixel of the image captured by the second camera which are situated on the second epipolar line:
   determining a second neighborhood being congruent to the first neighborhood;
   comparing intensity values of the first and second neighborhoods;
   determining a degree of consistency for the first and second neighborhoods;
   determining an image position of a pixel, on the second epipolar line having a highest degree of consistency;
   determining a position in space by means of the transformation based on the image position of the pixel of the first camera and the image position determined on the second epipolar line;
   storing the position in space; and
   determining the image of the object by a set of determined positions in space and being made available for further processing.

2. The method according to claim 1, which further comprises;
   inactivating a projection of the predetermined random image immediately before or after capturing the set of determined positions in space and that the objects to be imaged are additionally illuminated, at least one of the cameras capturing the image of the object to be imaged, an interpolated, intensity value or interpolated, intensity values of the image position, namely the image position of the pixel, by means of which the set of determined positions in space was/were determined based on the transformation being assigned to each of the set of determined positions in space.

3. The method according to claim 1, which further comprises portioning one of a surface or the space based on a number of space or surface elements by means of a meshing method based on a captured set of points.

4. The method according to claim 2, which further comprises assigning an intensity distribution, determined based on the intensity values of the points in space of the set of predetermined positions, including by interpolation, to the surface elements of the partitioned surface and displayed.

5. The method according to claim 1, which further comprises continuously capturing the three-dimensional images of the objects, that the objects are moved in relation to the cameras, relative movements being sufficiently slow to allow for an overlap of a captured area of space of two images subsequent in time, and that the sets of determined positions, partitioned surfaces or partitioned spaces are aligned by means of isometric transformation and, thus, an assembled image is obtained from a plurality of images.

6. The method according to claim 1, wherein that, in case of a lack of consistency between the first neighborhood and the second neighborhood of a second pixel on an epipolar line of the image captured by the second camera, a fluid matting a surface of the object to be imaged is sprayed onto the objects to be imaged and a procedure of determining consistent neighborhoods is continued after having sprayed on the fluid.

7. The method according to claim 1, which further comprises selecting the random image in a way that the pixels which are situated on the same epipolar line in the images captured by the two cameras have distinct neighborhoods.

8. The method according to claim 1, wherein the first neighborhood consists of 3×3 pixels or 5×5 pixels.

9. An assembly for capturing three-dimensional images of objects, the assembly comprising:
   two cameras having overlapping image areas;
   a projection unit for projecting a random image, individual pixels of the random image having one of at least two different color values and/or intensity values, and the random image being projectable into the overlapping image areas of said two cameras by said projection unit;
   a calibrating unit being post-positioned to said cameras, by means of said calibrating unit:
   positions and orientations of said two cameras in relation to one another and a transformation may be determined, the transformation assigning exactly one position in space, namely one voxel, in a three-dimensional image space each to an image position, namely a position of a pixel, of an image captured using a first of said cameras and an image position, namely a position of a pixel, of an image captured using a second of said cameras;
   a family of epipolar lines being determined for each of said cameras, exactly one epipolar line of said second camera being assigned to each of the epipolar lines of said first camera;
   an evaluation unit being post-positioned to said cameras, by means of said evaluation unit, for each pixel of the image captured by said first camera:
   a first neighborhood may be determined;
   a first epipolar line determined for said first camera and having a respective pixel may be determined;
   a second epipolar line of said second camera assigned to the determined first epipolar line may be determined, and for each pixel of the image captured by said second camera which are situated on the second epipolar line, a second neighborhood which is congruent to the first neighborhood may be determined;
   a comparing unit for comparing intensity values of the first and second neighborhoods, wherein:
   a degree of consistency for the first and second neighborhoods and the image position, namely of a pixel, on the second epipolar line having a highest degree of consistency may be determined by means of said comparing unit; and a transformation may be determined based on an image position of the pixel of said first camera and a determined image position on the second epipolar line by means of said comparing unit and that position in space may be stored in a memory.

10. The assembly according to claim 9, further comprising a light source, being switchable, and illuminating the overlapping image areas of said two cameras.

11. The assembly according to claim 9, further comprising an atomizer for applying an anti-shine fluid onto objects to be imaged.

12. The assembly according to claim 9, wherein said first and second cameras having optical axes that are almost parallel.

13. The assembly according to claim 9, wherein said two cameras and said projection unit are disposed on a same support or instrument.

14. The assembly according to claim 9, wherein the random image is selected so that the pixels located on the same epipolar line in the image captured by said two cameras have distinct neighborhoods.

15. The assembly according to claim 9, wherein said first neighborhood consists of 3×3 pixels or 5×5 pixels.

* * * * *